United States Patent [19]
Barnum

[11] Patent Number: 5,891,508
[45] Date of Patent: Apr. 6, 1999

[54] MASK FOR DISGUISING OR COUNTERACTING ODORS

[75] Inventor: Dennis Barnum, Portland, Oreg.

[73] Assignee: Portland State University, Portland, Oreg.

[21] Appl. No.: 871,454

[22] Filed: Jun. 9, 1997

[51] Int. Cl.[6] .................................................. B05D 3/02
[52] U.S. Cl. ............................... 427/2.31; 128/206.12; 128/206.19; 427/244; 427/385.5
[58] Field of Search ..................... 128/206.12, 206.19; 427/2.31, 244, 245, 385.5

[56] References Cited

U.S. PATENT DOCUMENTS 3,998,988  12/1976  Shimomai et al. ..................... 428/400
4,517,308   5/1985  Ehlenz et al. ......................... 502/401
5,636,628   6/1997  Barnum ............................. 128/206.12

*Primary Examiner*—Michael Lusignan
*Attorney, Agent, or Firm*—Glenna Hendricks; Stephen Gates

[57] ABSTRACT

Masks are produced which disguise or counteract strong odors that would ordinarily make the environment unpleasant. Masks are treated with a fixate carrier and at least one odor-masking or counteracting agent in a volatile solvent. In a preferred embodiment, both the inner and outer mask surfaces are essentially a continuous, homogeneous layer.

9 Claims, 1 Drawing Sheet

MASK FOR DISGUISING OR COUNTERACTING ODORS

FIELD OF THE INVENTION

This invention relates to masks for use in circumstances where undesirable odors present a problem. The masks of the invention are particularly appropriate for use by care-givers, laboratory personnel and industrial workers who must work in an environment where disagreeable odors are present.

BACKGROUND OF THE INVENTION

In caring for patients, the care-giver is often exposed to unpleasant odors which make the work environment unpleasant. The use of medications that have a strong odor or which cause the patient to exude an odor presents a real problem for health care workers, since it is not possible, by cleaning the environment, to avoid effects of such odors. One such medication is dimethylsulfoxide (DMSO), which is presently being used to treat a number of conditions, including closed head injuries. Health care workers required to work in the environment where these patients are treated find the odor quite objectionable and often intolerable.

In other instances, patients, because of their disease condition, exude an odor that is objectionable. It is difficult for both the health care worker and for the patient in such instances, since the worker who would like to give support-ive care has difficulty disregarding the odor which may actually be sufficiently objectionable to make to worker feel ill.

There are, additionally, many industrial and law-enforcement environments where workers are exposed to such strong odors that the workers may become ill. Such workers include morticians, pathologists, tannery workers, slaughter house workers, etc. The use of masks that would mitigate some of the unpleasantness in such work situations can greatly increase comfort and productivity of workers. Masks are made of several materials. However, protective masks are usually divided into two types: molded masks (which may be rigid or semirigid) and flexible masks. The masks may be made of woven or non-woven material which allows the ready passage of air. For purposes of the invention, either mask may be used.

U.S. Pat. No. 4,467,799 discloses a transparent odor-free face mask which has been treated with an odor-masking material. The odor-masking material is not mixed with a fixative and placed on an absorbent layer of material which acts as a support in the manner taught herein. While the structure of the mask is suggested, no particular odor-masking material is suggested or exemplified.

U.S. Pat. No. 4,503,851 discloses a mask which requires a sealed envelop impervious to volatile substances. The envelop which is sealed before use contains an odor-masking substance. When the seal of the envelop is removed and the mask is in use, the volatile substances mix with the air that is inhaled. In one instance, the mask has an aperture in the mask containing an envelop which is sealed on both outer and inner mask surfaces. When at least one seal on the envelop is broken, the volatile material in the envelop mixes with the air being inhaled when the face mask is in use. In another embodiment disclosed therein a mask having a woven cover has an envelop attached to the inside. That envelop has an absorbent layer that has been impregnated with a fragrance. The envelop has a layer that is perforated to allow the volatile material to evaporate. No use of any particular odor masking material is suggested therein. Only the structure of the mask itself is addressed in the patent.

Cain and Drexler (*Ann. NY Acad. Sci*, (1974) pp. 427–439) discuss the use of odors to counteract and mask odors, including additive effects and synergism.

SUMMARY OF THE INVENTION

Figure 1:
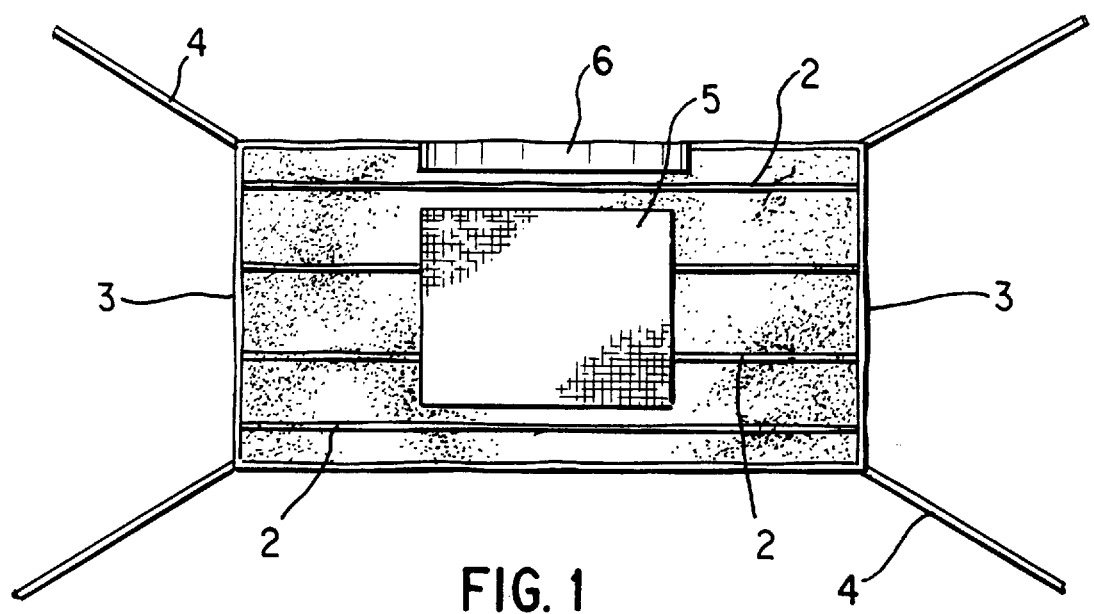
FIG. 1 shows a mask with a treated layer.

This invention provides a method of producing masks that mask and/or counteract strong odors that would ordinarily make work in the odoriferous environment quite unpleasant. Masks are made by (1) mixing a fixative carrier, a volatile solvent, and at least one odor masking and/or counteracting agent; (2) treating an absorbent material with the mixture obtained in step (1); and (3) allowing the volatile solvent to evaporate. Unlike the complex prior art masks, the masks of the invention have an absorbent layer over substantially the entire air intake area of the mask. Both the inner and outer mask surfaces are essentially a continuous, homogeneous layer. The odor masking and/or counteracting agent is applied in a fixative carrier. It is possible to make masks that provide a pleasant, relatively mild scent that will mask and/or counteract very strong odors. The masks of the invention provide long periods of effective use without annoyance from odor of the active agents. The masks disclosed herein retain their effectiveness during storage and use. The simplicity of structure of the novel masks results in production economies.

DETAILED DESCRIPTION OF THE INVENTION

The masks of this invention have at least one layer which comprises an absorbent material which covers substantially the entire the air intake area of the mask. The absorbent layer acts as a support for at least one odor masking/counteracting agent in a fixative carrier. In some instances, all layers of the mask are treated and so act as a support for the odor masking/counteracting agents and fixatives. The inner and outer surfaces of the masks are essentially a continuous, homogeneous layer. The masks of the invention were first designed for workers who were exposed to patients receiving dimethylsulfoxide. The odor produced during such therapy often is so intense and objectionable that workers can work with patients for only a limited period of time before they are overwhelmed by the odor. However, the masks of the invention are useful for many other purposes. The masks are useful for persons who are in close contact with patients suffering from diseases that cause the patient to exude objectionable odors. The masks are also useful in autopsy rooms, for law enforcement personnel and for persons working in odoriferous industrial environments.

The masks of the invention are prepared by making mixtures of carriers such as hydrogenated oil, wax, fat or polymeric carriers that act as fixatives for odor masking and/or counteracting agents. The fixative and odor masking/counteracting agents are dissolved in volatile solvent(s). (The term "fixative" as used herein refers to any material used to absorb or adsorb the odor masking/counteracting agent so that the odor-ameliorating component is released slowly when the mask is exposed to air, thereby prolonging the effectiveness of the odor mask.) The counteracting/masking agent with fixative and other additives in suitable solvent carriers may be applied to the masks by means known in the art including, for example, dipping, spraying, or flowing onto the absorbent material. Solvents used will depend on the materials used for odor amelioration and as fixatives and would include such solvents as ketones, alcohols, ethers, and hydrocarbons having boiling point less than about 100° C. Another solvent for use in high pressure spay guns is supercritical carbon dioxide (SCD). Use of SCD makes it possible to avoid use of solvents which may be flammable or which may present environmental problems. The masks are stored in air-tight containers such as plastic bags to retain the odor on the mask until use. Surprisingly, the odors used on the masks of the invention are not overwhelming to the wearer. However, the odor-ameliorating agents do effectively mask and/or counteract objectionable odors.

A distinction is made between "masking" and "counteracting" an odor. The term "masking" as used herein indicates that a fragrance, usually having a pleasant odor, is introduced. The intensity of the odor from the masking fragrance covers or modifies the objectionable odor or is so intense that it renders the objectionable odor imperceptible. The term "counteracting" as used herein indicates that the perceived intensity of the objectionable odor is lower or undetectable in the presence of the counteracting agent. The difference is that a counteracting substance may contribute little or no odor, though it reduces or eliminates the perception of the disagreeable odor. A fragrance may provide both masking and counteracting effects in any given application. The odors of fragrances exemplified herein are not overwhelming to the wearers of the masks. However, they do effectively ameliorate the unpleasant effects of the malodorous components in the air due to a combination of masking and counteracting effects. Masks of the invention may also contain bactericides. Some bactericides, such as cetyl trimethylammonium chloride, may be used to function both as fixatives and as bactericides.

Figure 2:
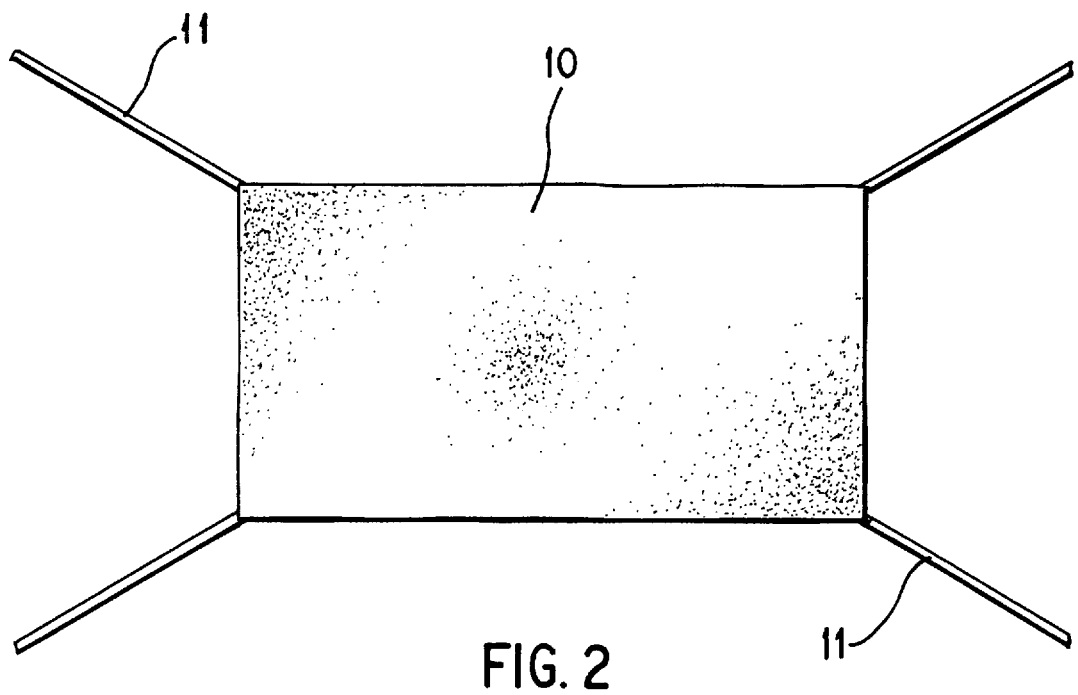
FIG. 2 shows a treated mask for use with a second mask which may be a specialized mask.

Both flexible and rigid or semi-rigid masks may be used for the purposes of the invention. In the health care setting, masks made of flexible materials which may be woven or non-woven may be more comfortable. However, desirability of any particular design will depend on the work situation and the personal preferences of the wearer. A very desirable design is pleated to provide flexibility over the nose and mouth with a hem or tape which holds pleats or gathers in place to impart desired shape to the mask. The top edge of the mask may have a strip of material such as metal in the upper hem or edging which facilitates firm fit over the nose. FIG. 1 shows a mask having pleats (2) wherein the pleats are held in place at the side with edging (3) which extends to provide ties (4) having a covering layer (5) of treated material. The top edging of the mask incorporates a strip (6) that can be shaped over the nose. FIG. 2 shows a mask containing material treated with odor masking/counteracting agent and fixative (10) having ties (11) which may be used with a rigid mask wherein the mask may be used with the mask as needed and may be placed within or over the mask. The placement of the treated layer will depend on whether or not the fragrance and/or fixative carrier is irritating to the skin. In many instances the entire mask may be treated.

It is essential that the layer containing the fragrance be made of absorbent material. Carriers for the fragrance may act as fixatives as well as carriers. Examples of such carriers include oils, glycols, waxes, hydrogenated vegetable oil or polymers of low volatility. Some agents that act as carriers have odor ameliorating effects of their own. For example, stearic acid is effective against the odor of ammonia, a odoriferous component of stale urine. The fixative carrier provides for slow release of the odor-masking/counteracting material. Provision of special pockets of fragrance that must be uncovered by removal of a seal before use is not cost effective. The odor-masking/counteracting material may be incorporated into the mask at manufacture. However, a mask containing the masking/counteracting agent in a carrier may be provided as an accessory that would be used with specialized masks such as those used to detoxify air containing toxic volatiles. A mask would, for example, be used directly against the face under specialized masks such as masks that receive air that has passed through a canister of detoxifying material. The mask used as a liner under the specialized mask can be made of a flexible material such as gauze and have gathers or pleats that allow expansion over the nose. Some of the masking/counteracting agents and fixative(s) may cause skin irritation. If such irritation occurs, a layer of material free of fragrance and fixative may be positioned between the fragrance-treated material and the skin.

Many kinds of carriers and odor masking/counteracting agents may be used. Several commercially available fragrances are exemplified. As an example, treated layers, made of absorbent cotton gauze or flannel 4×8 inches were used. As a further example, treated absorbent material can measure 7–8 inches square can be used. The sides are then pleated (2–4 pleats preferred) so that the mask is a rectangle with shorter sides about ⅓ to ½ the length of the top and bottom edges. The size and shape of the material treated will depend on particular design of the mask made.

Materials and Methods

Commercial sources of fragrances were Global Aromatics, Inc., Miami, Fla. and Benicia, Calif.; Felton International (now F & C Corporation) with offices in Allendale, Pa., and Prentiss Drug and Chemical Company, Floral Park, N.Y. The fragrances are identified by number and manufacturer. Abitol and Hercolyn-D were obtained from Global Aromatics, Benecia, Calif. Vancide-89RE was obtained from R.T. Vanderbilt Co., Norwalk, Conn. and Hyamine-3500 was obtained from Rohm and Haas, Philadelphia, Pa.

The masks were prepared as indicated in Example 1. To test the effectiveness of the odor masking and/or counteracting agents, the following solutions containing different concentrations of dimethylsulfide (DMS) in paraffin oil were prepared:

(A) $5.45 \times 10^{-3}$ molar (B) $2.18 \times 10^{-4}$ molar (C) $1.89 \times 10^{-5}$ molar The vapor over these solutions provides a range of concentrations of dimethylsulfide. Even the lowest concentration of dimethylsulfide is unpleasantly odiferous if a person is not wearing an odor mask.

To test the efficacy of a odor masking and/or counteracting agent, various volumes of fragrance were added to 5 mL portions of the above dimethylsulfide solutions in 4 dram vials. Usually 1–20 microliters of fragrance was added. After thorough mixing, the vapor over the solution was smelled (without a mask) and the results recorded as:

+=DMS smell of dimethylsulfide is detected

?=uncertain smell of dimethylsulfide

−=No odor of dimethylsulfide detected.

Some typical data are tabulated in Table I.

It was found that the method of testing described above wherein dimethylsulfide was combined with paraffin oil and fragrance provided a good means of predicting which fragrances would be effective for preparation of masks. As indicated in Table I, some of the cherry, lime and coconut fragrances were quite effective.

EXAMPLE 1

To prepare the solution for application to the mask, 3 grams of hydrogenated vegetable oil (CRISCO) was added to 50 mL of 30–60 petroleum ether followed by the addition of 10 $\mu$L Cherry fragrance (Felton #5173). After thorough mixing, a 4×8 inch cotton cloth (flannel) was placed on a glass plate and 3–5 milliliters of the petroleum ether/ CRISCO/fragrance mixture was poured onto the cloth. The petroleum ether flowed evenly over the cloth and evaporated within a few minutes leaving a dry cotton fabric impregnated with the vegetable oil and masking fragrance. The cloth was attached to the outside of a mask.

TABLE I

| Fragrance, Manufac., concentration. | DMS con A smell | DMSO con B smell | DMSO con C smell |
|---|---|---|---|
| Cherry, Felton #5173, 1 $\mu$L | + | − | − |
| Cherry, Felton #5791, 1 $\mu$L | + | + | ? |
| Cherry, Felton #5173 1 $\mu$L, Meelium 1 $\mu$L | + | − | − |
| Cherry, Felton #5791 1 $\mu$L, Meelium 1 $\mu$L | + | + | ? |
| Coconut, Felton #1171 1 $\mu$L | + | − | − |
| Coconut, Felton #1171 1 $\mu$L, Meelium 1 $\mu$L | + | − | − |
| Lemon, Felton #1818 1 $\mu$L | + | + | ? |
| Lemon, #1818 1 $\mu$L, Meelium 1 $\mu$L | + | + | − |
| Lime, Felton #2168 1 $\mu$L | + | + | ? |
| Lime, Felton #2169 1 $\mu$L | + | + | + |
| Orange, Felton #7991 1 $\mu$L | + | + | − |
| Shampoo Perfume, Felton #2006 1 $\mu$L | + | + | + |
| Vanilla, Felton #2838 + Meelium 1 $\mu$L | + | + | + |

Wherein:
con A = 5.45 × 10$^{-3}$ molal concentration DMS in paraffin oil
con B = 2.18 × 10$^{-4}$ molal concentration DMS in paraffin oil
con C = 1.89 × 10$^{-5}$ molal concentration DMS in paraffin oil Masks were prepared as indicated in Example 1. To test their effectiveness, solutions having different concentrations of dimethylsulfide in paraffin oil were placed in wide mouth 4 dram vials. Tests were made both with and without odor masks. If a person is not wearing an odor mask, even the lowest concentrations of dimethylsulfide in these solutions give an unpleasantly odiferous vapor. Table II shows some typical results while wearing odor masks. One mask was treated with lime (Felton M-2196) and the other with a cherry fragrance.

TABLE II

Effectiveness of odor masks against dimethylsulfide: Concentrations are moles of DMS per kilogram of paraffin oil × 10,000.

| Microliters of added fragrance | Molal concentration DMS × 10$^4$ | | | |
|---|---|---|---|---|
| | 1.85 | 4.60 | 11.9 | 79.4 |
| Lime (Felton M-2169) | | | | |
| 5 | − | − | n.d. | + |
| 10 | − | − | n.d. | n.d. |
| 20 | − | − | − | n.d. |
| Cherry (F&C 483172) | | | | |
| 5 | − | n.d. | + | + |
| 10 | − | − | n.d. | + |
| 20 | − | − | n.d. | + | wherein n.d. = no detectable odor.

Open air durability of the masks with fragrance was tested with 4×8 inches cotton cloth treated as indicated in Example 1. To test their effectiveness, solutions having different concentrations of dimethylsulfide in paraffin oil were prepared and placed in wide mouth 4 dram vials. Tests were made both with and without odor masks. If a person is not wearing an odor mask, vapors from even the lowest concentrations of dimethylsulfide in these dilutions are perceived as unpleasantly odiferous. Table II shows some typical results while wearing odor masks. The cloths were allowed to sit on a counter covered by a paper towel for several days to determine how long their effectiveness against the odor of dimethylsulfide would be retained. The more durable fragrances are still effective after two weeks.

To determine shelf life, 4×8 inch treated materials were placed in a closed plastic bag (Zip Lok) and allowed to remain on the shelf. After several months, the fragrance could still be readily detected and the masks were effective.

EXAMPLE 2

A solution is prepared as above, except that the fragrance is provided using 10 $\mu$L coconut (Global, #4190) and the fabric is an 8×8 inch piece of flannel. Ten mL of the fragrance in petroleum ether and CRISCO is poured over the flannel. The flannel is then placed over the outside surface of a piece of non-woven fabric and the sides of the flannel and non-woven fabric are pleated to provide a 4×8 inch rectangle. An edging is sewed along the long (unpleated) sides of the rectangle. Edging pieces 34 inches are cut and the center of the edging pieces are sewed along the pleated sides to hold the pleats in place and so that the edging pieces extend 15 inches beyond the mask edge at each corner to provide means for tying the mask to the face.

EXAMPLE 3

Masks of the invention were tested for mitigation of odors other than dimethylsulfide. To establish a scale of odor intensity a series of aqueous solutions containing increasing concentrations of the malodorous compound were prepared. The concentration range was selected to produce odor intensity varying from strong, objectionable odor to a solution so dilute that no odor could be detected. Odor intensities of the solutions constitute the standards by which other odors were compared. Molar concentration units were used. The air was bubbled through a solution so that the concentration of the malodorous compound is proportional to the concentration in the solution:

Concentration in air=k (Concentration in water) The proportionality constant, k, is approximately constant in the concentration range of the solutions. Thus, a ten-fold decrease in concentration of malodorous substance in the aqueous solution produces a ten-fold decrease in concentration in the gas phase. The standard odors were obtained by bubbling water-saturated air through the solution. The air stream was then passed through polytetrafluoroethylene (PTFE) tubing to a glass "Y" that split the air into two streams and directed it into each nostril. The intensity of odor was taken to be equal to the base ten logarithm of the molar concentration of malodorous compound in the aqueous standard. Because the odor intensity scale is logarithmic, an intensity of, for example, −3 corresponds to a concentration of malodorous substance ten times greater than −4 and one hundred times greater than −5.

To test an odor mask, the perception of the odor was compared with and without a mask. First, while wearing the mask, the odor intensity was noted. Then, without a mask, the concentration of aqueous solution producing the same intensity was determined. Several concentrations of odor were compared with each mask. For example, while wearing a mask, the odor intensity of air bubbled through a 10$^{-3}$ molar solution might be perceived to be equal to intensity of a $10^{-5}$ molar solution with no mask. The following data were recorded:

| Odor counteracted: | Pyridine |
| --- | --- |
| Counteractant: | Coconut #1171 fragrance |
| Fixative: | Hydrogenated Vegetable Oil |
| Bactericide: | None |

| | Odor intensity wearing mask | | |
| --- | --- | --- | --- |
| | Subject 1 | | Subject 2 |
| Odor Intensity w/o mask | Trial 1 | Trial 2 | (1 trail) |
| 0.0 | −1.5 | −0.5 | −1.0 |
| −0.5 | −1.5 | −1.0 | −1.3 |
| −1.0 | −2.0 | −1.5 | −2.0 |
| −1.5 | −2.5 | −2.5 | −3.0 |
| −2.0 | −3.5 | −3.5 | −3.5 |
| −2.5 | n.d. | −3.5 | n.d |
| −3.0 | n.d | n.d | n.d |

Odor intensity of −3.5 is barely detectable.
n.d. = no detectable odor.

| Odor counteracted: | Pyridine |
| --- | --- |
| Counteractant: | Coconut #1171 fragrance |
| Fixative: | Abitol |
| Bactericide: | None |

| | Odor intensity wearing mask |
| --- | --- |
| Odor Intensity w/o mask | Subject 1 |
| 0.0 | −1.0 |
| −0.5 | −1.5 |
| −1.0 | −2.5 |
| −1.5 | −2.5 |
| −2.0 | −3.5 |
| −2.5 | n.d. |
| −3.0 | n.d |

| Odor counteracted: | Pyridine |
| --- | --- |
| Counteractant: | Coconut #1171 fragrance |
| Fixative: | Hercolyn-D |
| Bactericide: | None |

| | Odor intensity wearing mask | |
| --- | --- | --- |
| Odor Intensity w/o mask | Subject 1 | Subject 2 |
| 0.0 | −1.0 | −1.0 |
| −0.5 | −1.0 | −1.5 |
| −1.0 | −2.0 | −2.5 |
| −1.5 | −2.5 | −3.5 |
| −2.0 | −3.0 | n.d. |
| −2.5 | −3.5 | |
| −3.0 | n.d | n.d |

| Odor counteracted: | Pyridine |
| --- | --- |
| Counteractant: | Coconut #1171 fragrance |
| Fixative: | Hercolyn-D |
| Bactericide: | Hyamine-3500 |

| | Odor intensity wearing mask | | |
| --- | --- | --- | --- |
| | Subject 1 | | Subject 2 |
| Odor Intensity w/o mask | Trial 1 | Trial 2 | (1 trail) |
| 0.0 | −1.0 | −3.0 | −1.0 |
| −0.5 | −1.5 | −3.5 | −1.5 |
| −1.0 | −2.0 | −3.5 | −2.0 |
| −1.5 | −2.5 | n.d. | −2.5 |
| −2.0 | −3.0 | n.d | −3.5 |
| −2.5 | n.d. | | |
| −3.0 | n.d | | n.d |

| Odor counteracted: | Pyridine |
| --- | --- |
| Counteractant: | Coconut #1171 fragrance |
| Fixative: | Hydrogenated Vegetable Oil |
| Bactericide: | Hyamine-3500 |

| | Odor intensity wearing mask |
| --- | --- |
| Odor Intensity w/o mask | Subject 1 |
| 0.0 | −1.0 |
| −0.5 | −1.5 |
| −1.0 | −2.0 |
| −1.5 | −3.0 |
| −2.0 | −3.5 |
| −2.5 | n.d. |
| −3.0 | n.d |

| Odor counteracted: | Pyridine |
| --- | --- |
| Counteractant: | Coconut #1171 fragrance |
| Fixative: | Hercolyn-D |
| Bactericide: | Vancide-89RE |

| | Odor intensity wearing mask | |
| --- | --- | --- |
| | Subject 1 | |
| Odor Intensity w/o mask | Trial 1 | Trial 2 |
| 0.0 | −1.0 | −2.0 |
| −0.5 | −1.0 | −2.0 |
| −1.0 | −1.5 | −2.5 |
| −1.5 | −2.0 | −2.5 |
| −2.0 | −2.5 | −3.5 |
| −2.5 | −3.0 | n.d. |
| −3.0 | −3.5 | |

| Odor counteracted: | Pyridine |
| --- | --- |
| Counteractant: | Coconut #1171 fragrance |
| Fixative: | Abitol |
| Bactericide: | Hyamine-3500 |

| | Odor intensity wearing mask | |
| --- | --- | --- |
| | Subject 1 | |
| Odor Intensity w/o mask | Trial 1 | Trial 2 |
| 0.0 | −1.0 | −2.0 |
| −0.5 | −1.5 | −3.0 |
| −1.0 | −2.0 | n.d. |
| −1.5 | −3.0 | |
| −2.0 | −3.5 | |
| −2.5 | n.d | |
| −3.0 | n.d | |

| Odor counteracted: | Pyridine |
| --- | --- |
| Counteractant: | Coconut #1171 fragrance |
| Fixative: | Abitol |
| Bactericide: | Vancide-89RE |

| | Odor intensity wearing mask | | |
| --- | --- | --- | --- |
| | Subject 1 | | |
| Odor Intensity w/o mask | Trial 1 | Trial 2 | Trial 3 |
| 0.0 | −1.0 | −2.0 | −2.0 |
| −0.5 | −1.5 | −3.0 | −2.5 |
| −1.0 | −2.0 | n.d. | −3.5 |
| −1.5 | −3.0 | | −3.5 |
| −2.0 | −3.5 | | n.d. |
| −2.5 | n.d. | | |

| Odor counteracted: | Pyridine |
| --- | --- |
| Counteractant: | Cherry #5173 fragrance |
| Fixative: | Hydrogenated Vegetable Oil |
| Bactericide: | None |

| | Odor intensity wearing mask |
| --- | --- |
| Odor Intensity w/o mask | Subject 1 |
| 0.0 | −0.5 |
| −0.5 | −1.5 |
| −1.0 | −1.5 |
| −1.5 | −2.0 |
| −2.0 | −3.0 |
| −2.5 | −3.5 |

-continued

| | |
|---|---|
| −3.0 | n.d. |
| −3.5 | n.d. |

| Odor counteracted: | Pyridine |
|---|---|
| Counteractant: | Lime #M2169 |
| Fixative: | Hydrogenated Vegetable Oil |
| Bactericide: | None |

| | Odor intensity wearing mask |
|---|---|
| Odor Intensity w/o mask | Subject 2 |
| 0.0 | −1. |
| −0.5 | −1.5 |
| −1.0 | −2.0 |
| −1.5 | −2.5 |
| −2.0 | −3.5 |
| −2.5 | n.d |
| −3.0 | |

| Odor counteracted: | 3-methylindole |
|---|---|
| Counteractant: | Coconut #1171 fragrance |
| Fixative: | Hydrogenated Vegetable Oil |
| Bactericide: | None |

| | Odor intensity wearing mask | |
|---|---|---|
| Odor Intensity w/o mask | Subject 1 | Subject 2 |
| −0.7 | −4.2 | |
| −1.2 | −4.2 | |
| −1.7 | n.d. | |
| −1.8 | | −2.8 |
| −2.2 | n.d. | |
| −2.3 | | −3.8 |
| −2.7 | n.d. | |
| −2.8 | n.d. | |

| Odor counteracted: | 3-methylindole |
|---|---|
| Counteractant: | Coconut #1171 fragrance + stearic acid |
| Fixative: | Stearic acid also acting as fixative |
| Bactericide: | None |

| | Odor intensity wearing mask | |
|---|---|---|
| Odor Intensity w/o mask | Subject 1 | Subject 2 |
| 0.7 | | −1.7 |
| −1.2 | | −2.7 |
| −1.7 | | −3.7 |
| −1.8 | | −4.2 |
| −2.2 | | n.d. |

| Odor counteracted: | 3-methylindole |
|---|---|
| Counteractant: | Coconut #1171 fragrance + stearic acid |
| Fixative: | Stearic acid also acting as fixative |
| Bactericide: | Hyamine |

| | Odor intensity wearing mask | |
|---|---|---|
| Odor Intensity w/o mask | Subject 1 | Subject 2 |
| −0.7 | | −1.7 |
| −1.2 | | −2.2 |
| −1.7 | | −3.2 |
| −1.8 | | −4.2 |
| −2.2 | | n.d. |

It was found that the combination of coconut #1171 fragrance with hydrogenated vegetable oil and Vancide-89 was overpowering. However, the substitution of the hydrogenated vegetable oil with Abitol or Hercolyn-D provided a useful mask. Coconut plus saturated vegetable oil with Hyamine had a strong odor, but that odor was not objectionable. Oil of citronella was also useful as a counteractant.

Masks of the invention were also useful against putrescene.

| Odor counteracted: | Putrescene |
|---|---|
| Counteractant: | Coconut #1171 fragrance + stearic acid |
| Fixative: | Stearic acid also acting as fixative |
| Bactericide: | None |

| | Odor intensity wearing mask | |
|---|---|---|
| Odor Intensity w/o mask | Subject 1 | Subject 2 |
| −0.0 | | −1.3 |
| −0.8 | | −2.3 |
| −1.3 | | −2.8 |
| −1.8 | | n.d. |
| −2.3 | | n.d. |

| Odor counteracted: | Putrescene |
|---|---|
| Counteractant: | Coconut #1171 fragrance + stearic acid |
| Fixative: | Hydrogenated Vegetable Oil |
| Bactericide: | Hyamine-3500 |

| | Odor intensity wearing mask | |
|---|---|---|
| Odor Intensity w/o mask | Subject 1 | Subject 2 |
| 0.0 | | −1.8 |
| −0.8 | | −2.3 |
| −1.3 | | −2.8 |
| −1.8 | | n.d. |
| −2.3 | | n.d. |

As indicated, it was found that several common commercial fragrances are quite effective at masking objectionable odor when the masks were prepared in accord with the teachings of the disclosure.

The method of testing disclosed above wherein dimethylsulfide was combined with paraffin oil and fragrance provided a relatively good means of predicting which fragrances would be effective for preparation of masks. As indicated, some of the cherry and coconut fragrances proved especially effective. The addition of meelium did not usually greatly effect ability of a fragrance to mask the odor of DMS. The coconut was particularly notable for its retention of effectiveness for several months.

The particular fragrances used in any instance may depend on the preferences of the target wearers. Some people may find particular odors more acceptable. For example, certain fragrances used in incense may be attractive to those from cultures where incense is used, while such fragrances might be objectionable to other populations.

The masks of the invention do not require that a sealed envelop be constructed in the mask to retain the masking/counteracting agent. The masks can be stored individually in air-impermeable packaging or severally in larger containers such as jars with covers.

I claim:

1. A method of preparing an odor mask comprising the steps of:
    (1) mixing a fixative carrier and an odor masking/counteracting agent;
    (2) treating an absorbent material with the mixture obtained in step (1); and
    (3) allowing the any volatile solvent used as a carrier for said fixative and said odor masking/counteracting agent that may be present to evaporate.

2. A method of claim 1 wherein the fixative carrier and fragrance are mixed with a volatile solvent before application to the absorbent material.

3. A method of claim 2 wherein the volatile solvent is a petroleum ether.

4. A method of claim 2 wherein the fixative is a fat, wax or oil.

5. A method of claim 2 wherein the fixative is a nonvolatile polymer.

6. A method of claim 5 wherein the fixative is a hydrogenated or partially hydrogenated vegetable oil.

7. A method of claim 2 wherein the odor masking/counteracting agent is a coconut fragrance.

8. A method of claim 2 wherein the odor masking/counteracting agent is a natural or synthetic fruit fragrance.

9. A method of preparing an odor mask comprising the steps of:

(1) mixing a carrier containing a fixative and an odor masking/counteracting agent;

(2) treating an absorbent material with the mixture obtained in step (1); and (3) allowing the any volatile solvent used as a carrier for said fixative and said odor masking/counteracting agent that may be present to evaporate.

* * * * *